United States Patent [19]
Shaw

[11] Patent Number: 5,357,982
[45] Date of Patent: Oct. 25, 1994

[54] PEDIATRIC LUMBAR PUNCTURE IMMOBILIZER

[76] Inventor: Fredrick C. Shaw, 221 S. Main St., Yazoo City, Miss. 39194

[21] Appl. No.: 982,387
[22] Filed: Jan. 25, 1993
[51] Int. Cl.$^5$ .............. A61B 19/00; A61G 15/00; A61G 7/06
[52] U.S. Cl. .................. 128/869; 128/845; 128/846; 5/621; 5/624
[58] Field of Search ............ 128/870, 869, 845; 606/240, 237; 5/603, 607, 621, 632, 652, 655, 657, 624

[56] References Cited

U.S. PATENT DOCUMENTS

| | | | |
|---|---|---|---|
| 4,584,730 | 4/1986 | Rajan | 5/632 |
| 5,096,173 | 3/1992 | Yamashita et al. | 5/621 |
| 5,113,875 | 5/1992 | Bennett | 128/845 |
| 5,180,386 | 1/1993 | Kennedy, Jr. | 128/845 |
| 5,189,748 | 3/1993 | Garrison et al. | 5/655 |
| 5,289,603 | 3/1994 | Kumagai | 5/621 |

Primary Examiner—Robert A. Hafer
Assistant Examiner—Michael O'Neill
Attorney, Agent, or Firm—Alexander Norcross

[57] ABSTRACT

A patient restraint, especially suited for pediatric patients, for securing and supporting the child during lumbar puncture procedures. A platform base supports the child on its side, acting as a lateral restraint. A padded mid-back support board, fixed to a bottom edge of the platform base, provides support for the lumbar region; an opening in the board provides access to the L4-L5 interspace region of the back. The child is clamped against this support board by a moveable padded abdominal stabilizer which is mounted on the platform base. A cervical support board is hinged to the mid-back support, and is fastened into an angled position to the mid-back support. A padded, triangular knee support is mounted to the base, at a position along a positioning groove which is inwardly angled from the bottom edge of the base, so that as the knee support moves inwardly, it moves upwardly. A child positioned against the mid-back support is secured by clamping the abdominal stabilizer against the child, holding its lower body and pelvis fixed against the mid-back support in proper position to expose the L4-L5 interspace. The spine is then tensioned by bending up the cervical stabilizer, flexing the upper back into the desired curved position, and also raising the knee stabilizer to bend and hold the legs in a bent position, thus approximating the desired fetal position.

3 Claims, 2 Drawing Sheets

PEDIATRIC LUMBAR PUNCTURE IMMOBILIZER

BACKGROUND OF THE INVENTION

This patent relates to the field of medical apparatus for immobilizing patients, especially pediatric patients.

A particular need exists for immobilizing a patient when performing a procedure which requires exact placement of an invasive probe or needle; this is particularly important when such placement includes the risk of serious injury or damage from an inadvertent motion of the patient. Notable among such procedures are spinal tap or lumbar puncture procedures, involving the insertion of a needle into the spinal canal through the spaces between lumbar vertebrae; any motion of the patient while the needle is inserted runs a serious risk of spinal damage. Since spinal taps are very uncomfortable, the risk of such motion is particularly severe in children.

Several patient immobilizers have been developed for holding small children in a proper position for a spinal tap. Such immobilizers usually involve strapping the child into a rigid position.

U.S. Pat. No. 3,829,079 discloses a patient immobilizer in which two angled, opposed pads bear against the cervical-occipital and posterior thigh areas to maintain a patient in an essentially bowed, fetal position The pads are mounted at the ends of telescoping shafts, which are secured only at one end.

U.S. Pat. No. 4,620,535 shows an infant immobilizer which is an anchor plate with straps attached, the straps securing the ankles, wrists, and cervical area of the infant to position the infant in a bent spine position for a spinal tap.

U.S. Pat. No. 4,732,145 shows a spinal tap immobilizer in which the patient is positioned over a fixed V-shaped frame, and held in position on the frame by wrist, ankle and neck straps.

U.S. Pat. No. 4,223,670 discloses a spinal tap restraint in the form of a flexible panel with a plurality of straps to restrain the legs and arms from motion, while securing the body in a suitably bent posture.

Other patient immobilizers are known. U.S. Pat. No. 3,223,084 discloses an immobilizer in which the patient lies on a supporting platform from which rises, on a post, a pelvic clamp which is lowered, clamping the pelvis and thighs. This patent notes that pediatric patients may exhibit fear and hysteria when excessively confined. Children further exhibit a squirming motion when the pelvic region is not restrained from turning or rotation.

U.S. Pat. No. 3,672,364 discloses a patient restraint in which opposed pads are positioned by means of straps to a bed to provide orthopedic tension.

U.S. Pat. No. 4,578,833 discloses an oscillating hospital bed in which a child may be secured by opposed support packs, mirror images of one another, which are positioned by a bracket, comprising two flat strips joined by a hand screw. These supports are used in conjunction with straps about the patient.

U.S. Pat. No. 3,844,550 discloses a pelvic immobilizer in which opposing plates, one fixed to a platform to support the back of a patient, and the other sliding against the front of the patient, with padded supports engaging the two pelvic bones, serve to clamp and immobilize the pelvis against significant forces.

SUMMARY OF THE INVENTION

The invention is a patient restraint, especially suited for pediatric patients, for securing and supporting the child during lumbar puncture procedures.

Lumbar puncture procedures, which are required for obtaining spinal fluid samples for diagnostic procedures, present a risk of damage to the patient's spinal cord if any movement of the patient occurs. Such procedures are done without anesthesia; compounding the problem of unwanted movement in children is the possibility of the puncture instrument contacting the spinal nerves, causing an involuntary reflex response.

Securing a child against movement requires that the apparatus positively secure the child against both response to pain, and to involuntary muscle reflex responses. However such restraints cannot be of the type that so bind the child that a panic response ensues, or that unduly heightens the fears of the child.

The invention is a supporting platform base, which may be placed on a table; for a typical child the base is two feet square. This base supports the child on its side, acting as a lateral restraint. A padded mid-back support board, fixed to a bottom edge of the platform base, provides support for the lumbar region; an opening in the board provides access to the L4-L5 interspace region of the back. The child is clamped against this support board by a moveable padded abdominal stabilizer which is mounted on the platform base by a through rod and wing nut in a positioning groove which is perpendicular to the bottom edge of the base.

A cervical support board is hinged to the mid-back support, and is fastened into an angled position to the mid-back support by another rod and wing nut passing through a positioning groove which is angled to the mid-back support. A padded, triangular knee support is mounted to the base, at a position along a positioning groove which is inwardly angled from the bottom edge of the base, so that as the knee support moves inwardly, it moves upwardly.

A child positioned against the mid-back support is secured by clamping the abdominal stabilizer against the child, holding its lower body and pelvis fixed against the mid-back support in proper position to expose the L4-L5 interspace. The spine is then tensioned by bending up the cervical stabilizer, flexing the upper back into the desired curved position, and also raising the knee stabilizer to bend and hold the legs in a bent position. Thus approximating the desired fetal position.

The clamping effect of the three movable stabilizers, all perpendicular to the platform base, secures the child against both lateral and bending motion; nevertheless, the padded stabilizers, which do not require wrist straps or ankle straps, do not cause the child to feel trapped, and thus avoids panic in the child. There is significantly less patient discomfort form the apparatus than for some prior art restraints.

It is thus an object of the invention to disclose a pediatric patient immobilizer which is particularly suited to lumbar puncture procedures.

It is a further object of the invention to disclose a pediatric patient immobilizer which secures the patient against both lateral and bending motions.

It is a further object of the invention to disclose a pediatric patient immobilizer which reduces the discomfort and fear experienced by a child when restrained.

It is a further object of the invention to disclose a pediatric patient immobilizer which does not induce panic reactions in a child when restrained.

It is a further object of the invention to disclose a pediatric patient immobilizer which safely secures a child without requiring several nurses or attendants to hold the child.

It is a further object of the invention to disclose a pediatric patient immobilizer which may be used for a wide range of sizes of patients.

These and other objects of the invention may be seen form the detailed description of a preferred embodiment of the invention which follows.

DETAILED DESCRIPTION OF THE INVENTION

Figure 1:
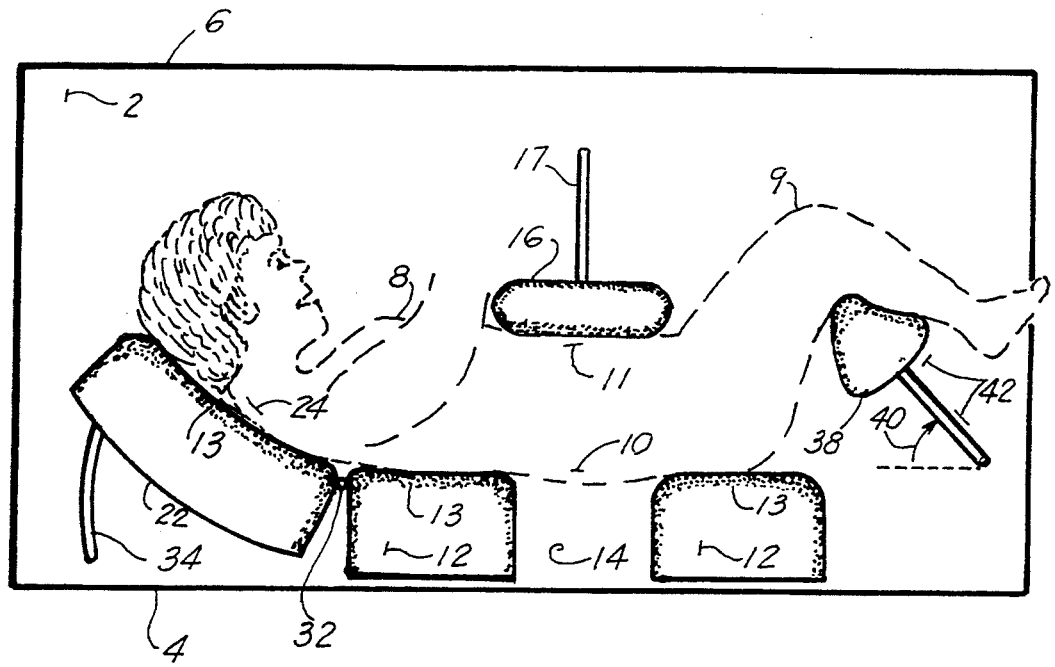
FIG. 1 is a view from above of the invention with a child positioned therein.
Figure 2:
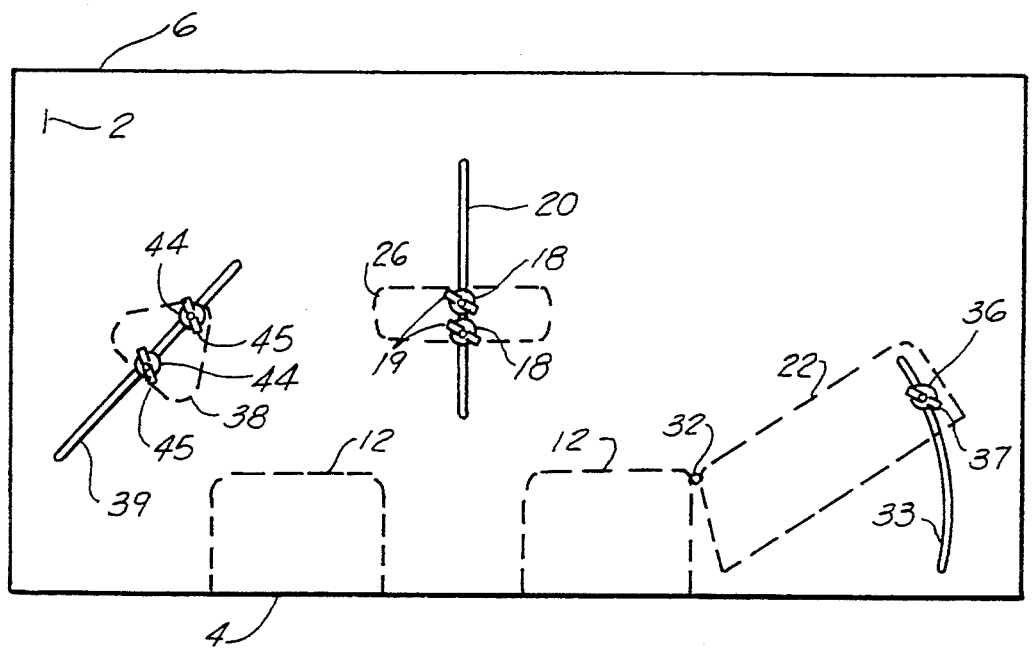
FIG. 2 is a bottom view of the platform base of the invention.
Figure 3:
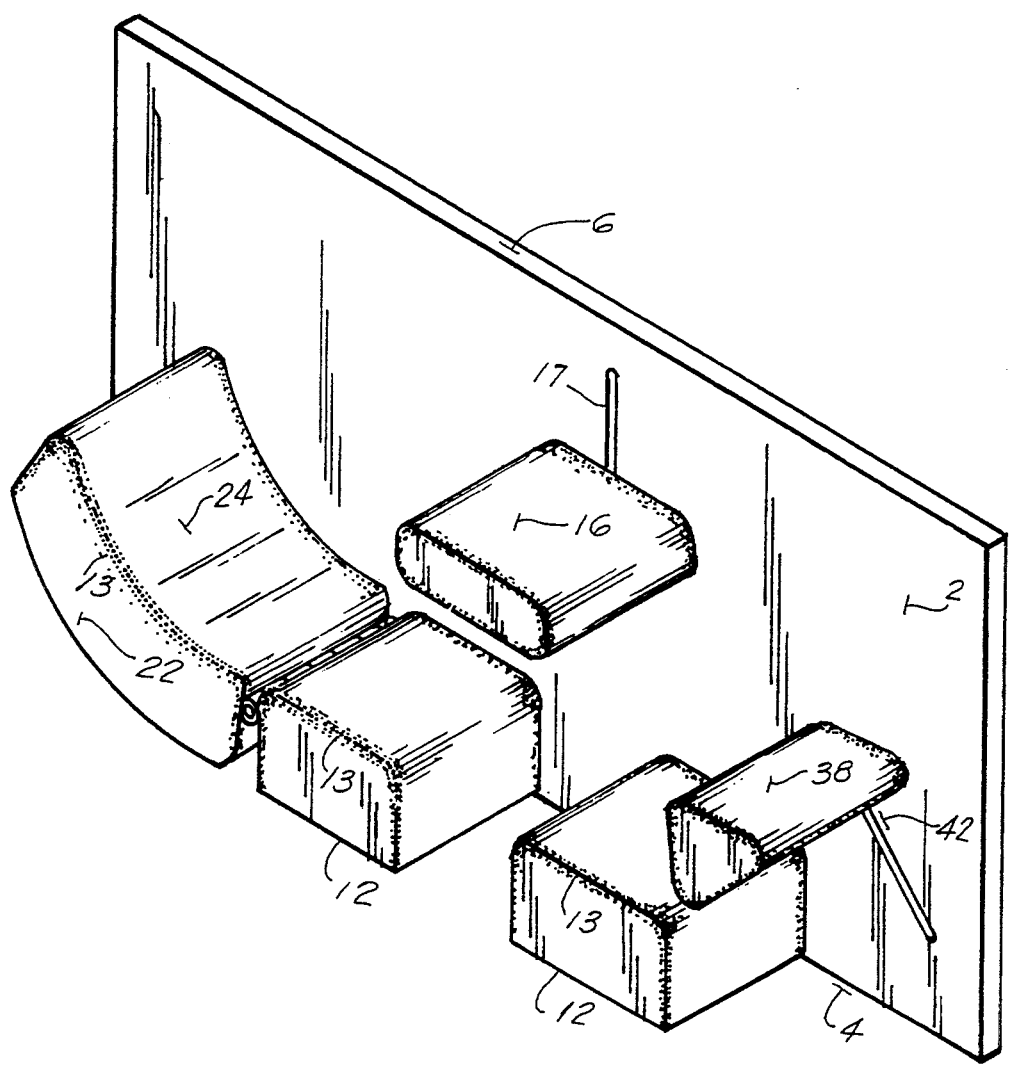
FIG. 3 is an angled view of the invention.
Figure 4:
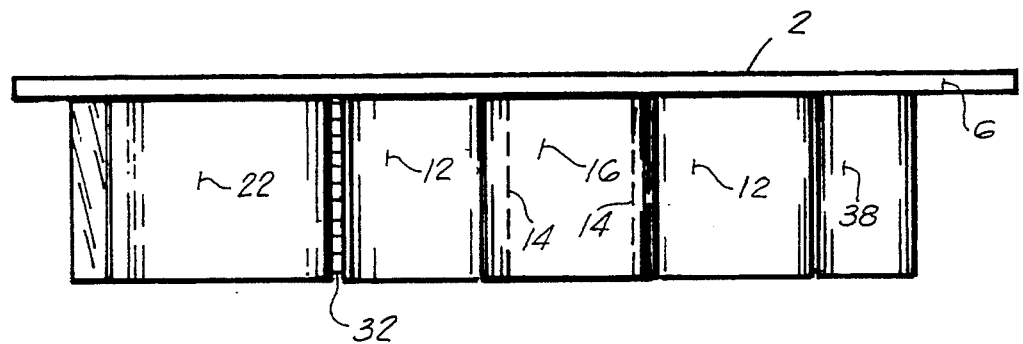
FIG. 4 is a view from the top edge of the platform base of the invention.

The invention is constructed of a platform base 2 which is a flat board, of a size convenient to place on an operating table. For a small child, a typical size will be three feet wide by two feet high. For the remaining description, the board is described as though it had a bottom edge 4 and a top edge 6, thus defining the directions up and down on the platform base 2. These are merely figurative directions as the platform base 2 is actually placed horizontal when in use.

Perpendicularly mounted on the bottom edge 4 of the base 2 is a mid-back support 12. Mid-back support 12 is a padded board, preferably covered with a foam pad for comfort, the foam pad then being covered with an impervious, easily cleaned surface such as vinyl or leather, to form a protective padding 13. The length of Mid-back support 12 is adapted to support the lumbar region 10 of a child 8 when that child 8 is positioned, lying on its side on the platform base 2. Within mid-back support 12 is provided a lumbar opening 14, an essentially rectangular opening which is positioned so as to give access to the inter-vertebra spaces between the third lumbar vertebra (L3) down to the fifth lumbar vertebra (L5), when the child is positioned as stated above.

Mounted Perpendicularly to the base 2 is a padded abdominal stabilizer 17. Abdominal stabilizer 17 is a substantially rectangular board, mounted in opposing juxtaposition to mid-back support 12, and provided with means 16 for positioning the abdominal stabilizer 17 at any position along a line perpendicular to the mid-back support, so that the abdominal stabilizer 17 can be moved into or away from the mid-back support 12. Abdominal stabilizer 17 is padded and covered 13 in the same manner as described above for mid-back support 12.

Means for positioning 16 for abdominal stabilizer 17 in the preferred embodiment shown comprises a straight slot or groove 20 in the base 2 which extends along the path of desired motion of the stabilizer 17. Since this path for abdominal stabilizer 17 is into or away form mid-back support 12, the slot 20 is perpendicular to the bottom edge 4 of the base 2. Abdominal stabilizer 17 is secured at any position along the slot 20 by means of one or two threaded rods 18 extending down from the stabilizer 17 through the slot 20; these rods 19 are secured by hand tightening nuts 19 to the base 2. These nuts 19 may preferably be wing nuts, or any form of fastener which is easily tightened by hand.

An alternative means of positioning 16 is a series of holes along a line perpendicular to bottom edge 2, sized to accept support rods mounted in the bottom of abdominal stabilizer 17, which can then be positioned by placement is any of the chosen holes. Other positioning means will naturally occur to the skilled constructor, and will be suitable so long as such means permits ready adjustment of the position of the stabilizer by the practitioner, and then rigid fixation of the stabilizer in the position chosen against any possible force exerted by the child.

A cervical support board or stabilizer 22 is affixed to the mid-back support 12 by a hinged joint 32. Cervical stabilizer 22 preferably has an inward curve 24. Cervical stabilizer 22 has means for positioning 34 which position the Cervical stabilizer 22 at any chosen angle with respect to mid-back support 12. These means for positioning 34 in the preferred embodiment comprise a slot 35 in base 2, which may be curved or angled, and at least one rod 36 extending down from Cervical stabilizer 22 through slot 35 to be secured against base 2 by a nut 37. As with abdominal stabilizer 16, Cervical stabilizer 22 has a covered padding 13, and may have many alternate means for positioning 34.

A knee stabilizer or brace 38 is mounted to the base 2 by means for positioning 42 which permit the knee stabilizer 38 to be moved at an inward angle 40 with respect to mid-back support 12. This inward angle 40 results in the knee stabilizer 38 being moveable from a position near the bottom edge 4 of the base 2 on an inward and upward direction. As with the abdominal stabilizer 16, knee stabilizer 38 is, in the preferred embodiment, positioned by means of rods 44 extending form the bottom of knee stabilizer 38 down through a slot 39 in the base 2, and secured to the base 2 by means of hand tightening nuts 45 on the rods 44. As above described, this is only one of several ways for constructing means for positioning 42.

In use, a child 8 is positioned on its side on the base 2, positioned so that its lumbar region 10 is against the mid-back support 12. The abdominal stabilizer 16 is then positioned tightly against the child's abdominal region 11, clamping the child against the mid-back support. Since all surfaces in contact with the child are padded, then child has minimal discomfort from this procedure.

The child's spinal column is thus positioned in a stable horizontal and vertical position by the side support provided by the base 2 in conjunction with the back support provided by the combination of the mid-back support 12 and the clamping pressure exerted by the abdominal stabilizer 16. The child's knees 9 are raised to a near fetal position, bracing the legs against the padded abdominal stabilizer 16, by positioning the knee stabilizer 38 into the knees as for as may comfortably be done.

This positioning of the knee stabilizer 38 also serves to stretch the spinal column. The full extension of the spinal column for lumbar puncture is accomplished by flexing the upper lumbar and cervical spine forward by positioning the cervical stabilizer 22 at an angle with respect to the mid-back support 12. Again, all stabilizers being padded, this positioning is done at minimal discomfort to the patient. However the resulting position of the patient produces the desired bent spine position which provides maximal space between the lumbar vertebra for most efficient and effective insertion of a spinal needle. The lumbar opening 14 in the mid-back support 12 provides ready operative access to the L3 to L5 interspaces for lumbar puncture; the patient 8 is fully secured against motion by the combined stabilizer clamping and the lateral support of the platform base 2 against the patient's side. The patient 8 is fully visible to the physician during the procedure, as the apparatus does not, unlike prior art supports, conceal the patient's respiration and reactions from the physician's view.

The invention will firmly support the child, comfortably positioning it in a fashion which is ideal for performing a lumbar puncture procedure. Since the patient is supported laterally by lying on his/her side on the platform base, and secured by the clamping effect of the abdominal stabilizer against the mid-back support, there is good horizontal and vertical alignment of the spinal column. At the same time there is maximal separation of the L3-L4-L5 interspaces for placement of the spinal needle. This separation of the interspaces is created by the locked, angled positioning of the cervical stabilizer which maintains the upper half of the back and the neck in a flexed forward position.

It can readily be seen that the invention, when a patient is positioned for lumbar puncture, with stabilizers locked in place, has significant advantages:

The padded covered stabilizers provide a firm but comfortable positioning support for the patient. The need for one or two nurses to hold the child is eliminated. The accurate positioning of the spinal column increases the accuracy, ease and efficiency of needle placement and thus of the spinal tap procedure.

Most important, the danger to an otherwise wiggling or frantic child is reduced by stabilizing that child's position.

And, unlike securing devices which essentially fold up a child, the physician is able to cleanly observe the patient's respirations during the entire procedure.

It can readily be seen that the exact padding and covering of the apparatus, and the actual means for positioning and locking the moveable stabilizers may be varied over a wide range by those of skill in the art. This invention therefore is not restricted to the exact embodiment disclosed, but extends to the wider equivalents inherent in the claims.

I claim:

1. An Immobilizer for positioning a patient for lumbar puncture comprising:
    a flat platform base;
    a mid-back support, extending from an edge of, perpendicular to, said platform base, having therein an opening for spinal access;
    a cervical stabilizer, pivotally attached to an end of said mid-back support, extending from and perpendicular to said platform base, with means for fixing the position thereof at a chosen angle to said mid-back support, at a position on said platform base;
    an abdominal stabilizer, extending from said platform base, opposingly facing said mid-back support, with means for fixing the position thereof on said platform base, opposingly spaced from said mid-back support;
    a knee stabilizer, extending from said platform base, with means for fixing the position thereof on said platform base with respect to said mid-back support.

2. The apparatus of claim 1, said means for fixing the position of said stabilizers comprising:
    an extended slot in said platform base;
    a threaded support rod extending from said stabilizer through said slot, and
    a manually fastened nut securing said rod against said platform base.

3. The apparatus of claim 1 said cervical stabilizer comprising:
    a board, one end hinged to said mid-back support, said board being curved inwardly with respect to said mid-back support.

* * * * *